(12) United States Patent
Andree et al.

(10) Patent No.: US 6,175,010 B1
(45) Date of Patent: *Jan. 16, 2001

(54) 3-AMINO-1-CYANOPHENYL-URACILS

(75) Inventors: Roland Andree; Mark Wilhelm Drewes, both of Langenfeld (DE); Markus Dollinger, Overland Park, KS (US)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/319,280
(22) PCT Filed: Nov. 27, 1997
(86) PCT No.: PCT/EP97/06618
  § 371 Date: Jun. 2, 1999
  § 102(e) Date: Jun. 2, 1999
(87) PCT Pub. No.: WO98/25909
  PCT Pub. Date: Jun. 18, 1998

(30) Foreign Application Priority Data

Dec. 9, 1996 (DE) .............................. 196 51 036

(51) Int. Cl.⁷ .................. C07D 239/54; A01N 43/54
(52) U.S. Cl. ...................... 544/310; 544/310; 544/311
(58) Field of Search ..................... 504/243; 544/310, 544/311

(56) References Cited

U.S. PATENT DOCUMENTS 5,266,554  11/1993  Suchy et al. ................ 504/243

FOREIGN PATENT DOCUMENTS

4440914     *  5/1996  (DE).
196/ 04 229     8/1996  (DE).
0473551     *  3/1992  (WO).
WO 95/06641 *  3/1995  (WO).

* cited by examiner

Primary Examiner—Mukund J. Shah
Assistant Examiner—Hong Liu
(74) Attorney, Agent, or Firm—Joseph C. Gil

(57) ABSTRACT

Novel 3-amino-1-cyanophenyl-uracils of the formula

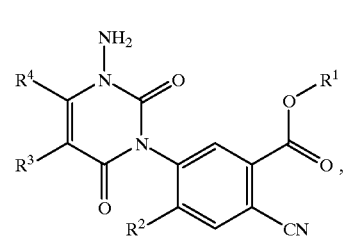

(I)

in which $R^1$ represents hydrogen or represents in each case optionally substituted alkyl, alkenyl, alkinyl, cycloalkyl, cycloalkylalkyl, aryl, arylalkyl, heterocyclyl or heterocyclylalkyl, $R^2$ represents hydrogen, cyano or halogen, $R^3$ represents hydrogen, halogen or optionally substituted alkyl, $R^4$ represents optionally substituted alkyl, a process for their preparation and their use as herbicides.

5 Claims, No Drawings

3-AMINO-1-CYANOPHENYL-URACILS

TECHNICAL FIELD OF THE INVENTION

The present invention relates to novel 3-amino-1-cyanophenyl-uracils, to a process for their preparation and to their use as herbicides.

BACKGROUND OF THE INVENTION

It is already known that certain 3-alkyl-1-cyanophenyl-uracils have herbicidal properties (cf. EP-A 0 473 551). Thus, for example, isopropyl 2-cyano-5-[3,6-dihydro-2,6-dioxo-3-methyl-4-trifluoromethyl-1(2H)-pyrimidinyl]-4-fluoro-benzoate can be used for controlling weeds. However, at low application rates, the efficacy of this substance is not always satisfactory.

DETAILED DESCRIPTION OF THE INVENTION

This invention, accordingly, provides novel 3-amino-1-cyano-phenyl-uracils of the formula

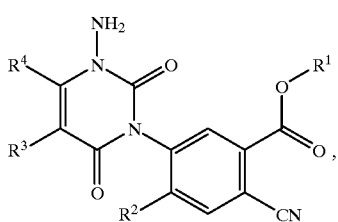

(I)

in which
$R^1$ represents hydrogen or represents in each case optionally substituted alkyl, alkenyl, alkinyl, cycloalkyl, cycloalkylalkyl, aryl, arylalkyl, heterocyclyl or heterocyclylalkyl,
$R^2$ represents hydrogen, cyano or halogen,
$R^3$ represents hydrogen, halogen or optionally substituted alkyl,
$R^4$ represents optionally substituted alkyl.

Furthermore, it has been found that 3-amino-1-cyanophenyl-uracils of the formula (I) are obtained when 1-cyanophenyl-uracils of the formula

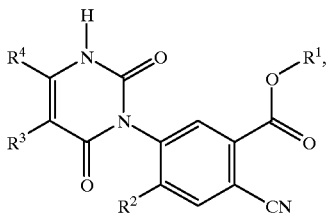

(II)

in which
$R^1$, $R^2$, $R^3$ and $R^4$ are each as defined above,
are reacted with an electrophilic aminating agent,
if appropriate in the presence of an acid binder and if appropriate in the presence of a diluent.

Finally, it has been found that the novel 3-amino-1-cyanophenyl-uracils of the formula (I) have very good herbicidal properties.

Surprisingly, the 3-amino-1-cyanophenyl-uracils of the formula (I) according to the invention have considerably better herbicidal activity than isopropyl 2-cyano-5-[3,6-dihydro-2,6-dioxo-3-methyl-4-trifluoromethyl-1(2H)-pyrimidinyl]-4-fluoro-benzoate, which is a prior-art active compound of similar constitution and the same direction of action.

In the definitions, the saturated or unsaturated hydrocarbon chains, such as alkyl, alkenyl or alkinyl, are in each case straight-chain or branched.

Halogen generally represents fluorine, chlorine, bromine or iodine, preferably represents fluorine, chlorine or bromine, in particular represents fluorine or chlorine.

The formula (I) provides a general definition of the 3-amino-1-cyanophenyl-uracils according to the invention. Preference is given to compounds of the formula (I) in which
$R^1$ represents hydrogen or represents optionally cyano-, carboxyl-, halogen-, $C_1-C_4$-alkoxy- or $C_1-C_4$-alkoxy-carbonyl-substituted alkyl having 1 to 6 carbon atoms or represents in each case optionally cyano-, carboxyl- or $C_1-C_4$-alkoxy-carbonyl-substituted alkenyl or alkinyl having in each case 2 to 6 carbon atoms, or
represents cycloalkyl or cycloalkylalkyl having in each case 3 to 6 carbon atoms in the cycloalkyl group and optionally 1 to 4 carbon atoms in the alkyl moiety and being in each case optionally mono- to tetrasubstituted by identical or different substituents selected from the group consisting of cyano, carboxyl, halogen, $C_1-C_4$-alkyl and $C_1-C_4$-alkoxy-carbonyl, or represents aryl or arylalkyl having 6 or 10 carbon atoms in the aryl group and optionally 1 to 4 carbon atoms in the alkyl moiety and being in each case optionally mono- to trisubstituted by identical or different substituents selected from the group consisting of nitro, cyano, carboxyl, halogen, $C_1-C_4$-alkyl, halogeno-$C_1-C_4$-alkyl, $C_1-C_4$-alkoxy, halogeno-$C_1-C_4$-alkoxy and/or $C_1-C_4$-alkoxy-carbonyl, or
represents heterocyclyl or heterocyclylalkyl from the series oxetanyl, furyl, furylmethyl, tetrahydrofuryl, tetrahydrofurylmethyl, thienyl, oxazolyl, isoxazolyl, thiazolyl, pyrazolyl, oxadiazolyl, pyridinyl, pyridinylmethyl, each of which is optionally mono- to trisubstituted by identical or different substituents selected from the group consisting of cyano, carboxyl, halogen, $C_1-C_4$-alkyl, halogeno-$C_1-C_4$-alkyl, $C_1-C_4$-alkoxy and/or halogeno-$C_1-C_4$-alkoxy,
$R^2$ represents hydrogen, cyano, fluorine, chlorine or bromine,
$R^3$ represents hydrogen, fluorine, chlorine, bromine or represents alkyl having 1 to 4 carbon atoms which is optionally mono- to pentasubstituted by identical or different substituents selected from the group consisting of fluorine, chlorine and bromine, and
$R^4$ represents alkyl having 1 to 4 carbon atoms or represents halogenoalkyl having 1 to 4 carbon atoms and 1 to 5 fluorine, chlorine and/or bromine atoms.

Particular preference is given to compounds of the formula (I) in which
$R^1$ represents hydrogen or represents optionally cyano-, carboxyl-, fluorine-, chlorine-, methoxy-, ethoxy-, propoxy-, methoxycarbonyl-, ethoxycarbonyl- or propoxycarbonyl-substituted methyl, ethyl, n- or i-propyl, n-, i-, s- or t-butyl, or
represents in each case optionally cyano-, carboxyl-, methoxycarbonyl- or ethoxycarbonyl-substituted propenyl, butenyl, propinyl or butinyl, or
represents cyclopropyl, cyclobutyl, cyclopentyl, cyclohexyl, cyclopropylmethyl, cyclobutylmethyl, cyclopentylmethyl or cyclohexylmethyl, each of which is optionally mono- to tetrasubstituted by identical or different substituents selected from the group consisting of cyano, carboxyl, fluorine, chlorine, methyl, ethyl, methoxycarbonyl and ethoxycarbonyl, or represents phenyl or benzyl, each of which is optionally mono- to trisubstituted by identical or different substituents selected from the group consisting of nitro, cyano, carboxyl, fluorine, chlorine, methyl, ethyl, trifluoromethyl, methoxy, ethoxy, difluoromethoxy, trifluoromethoxy, methoxycarbonyl and ethoxycarbonyl, or represents heterocyclyl or heterocyclylalkyl from the series oxetanyl, furyl, furylmethyl, tetrahydrofuryl, tetrahydrofurylmethyl, thienyl, oxazolyl, isoxazolyl, thiazolyl, pyrazolyl, oxadiazolyl, pyridinyl, pyridinylmethyl, each of which is optionally mono- to trisubstituted by identical or different substituents selected from the group consisting of cyano, carboxyl, fluorine, chlorine, methyl, ethyl, trifluoromethyl, methoxy, ethoxy, difluoromethoxy and trifluoromethoxy, $R^2$ represents hydrogen, fluorine or chlorine, $R^3$ represents hydrogen, fluorine, chlorine, methyl, ethyl or represents halogenoalkyl having 1 or 2 carbon atoms and 1 to 3 fluorine and/or chlorine atoms and $R^4$ represents methyl, ethyl or represents halogenoalkyl having 1 or 2 carbon atoms and 1 to 5 fluorine and/or chlorine atoms.

The abovementioned general or preferred radical definitions apply both to the end products of the formula (I) and also, correspondingly, to the starting materials or intermediates required in each case for the preparation. These radical definitions can be combined with each other at will, i.e. including combinations between the given preferred ranges.

Examples of the compounds of the formula (I) according to the invention are listed in the groups below.

Group 1

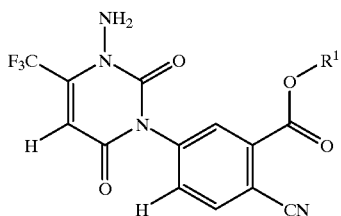

(Ia)

$R^1$ here has the following meanings:
hydrogen, methyl, ethyl, n- or i-propyl, n-, i-, s- or t-butyl, n-, i-, s- or t-pentyl, fluoroethyl, chloroethyl, chlorofluoroethyl, difluoroethyl, dichloroethyl, trifluoroethyl, trichloroethyl, chlorodifluoroethyl, fluoropropyl, chloropropyl, difluoropropyl, dichloropropyl, trifluoropropyl, trichloropropyl, cyanoethyl, cyanopropyl, cyanobutyl, carboxymethyl, carboxyethyl, carboxypropyl, carboxybutyl, methoxymethyl, ethoxymethyl, propoxymethyl, methoxyethyl, ethoxyethyl, propoxyethyl, methoxypropyl, ethoxypropyl, propoxypropyl, methoxycarbonylmethyl, ethoxycarbonylmethyl, propoxycarbonylmethyl, methoxycarbonylethyl, ethoxycarbonylethyl, propoxycarbonylethyl, methoxycarbonylpropyl, ethoxycarbonylpropyl, propoxycarbonylpropyl, 1-propen-3-yl (allyl), 3-methyl-1-propen-3-yl, 2-buten-4-yl (crotonyl), 1-propin-3-yl (propargyl), 3-methyl-1-propin-3-yl, 2-butin-4-yl, cyclopropyl, cyanocyclopropyl, carboxycyclopropyl, difluorocyclopropyl, dichlorocyclopropyl, methylcyclopropyl, methoxycarbonylcyclopropyl, ethoxycarbonylcyclopropyl, cyclobutyl, cyanocyclobutyl, carboxycyclobutyl, difluorocyclobutyl, trifluorocyclobutyl, tetrafluorocyclobutyl, chlorotrifluorocyclobutyl, methylcyclobutyl, cyclopentyl, cyanocyclopentyl, carboxycyclopentyl, fluorocyclopentyl, chlorocyclopentyl, difluorocyclopentyl, dichlorocyclopentyl, methylcyclopentyl, methoxycarbonylcyclopentyl, ethoxycarbonylcyclopentyl, cyclohexyl, cyanocyclohexyl, carboxycyclohexyl, fluorocyclohexyl, chlorocyclohexyl, difluorocyclohexyl, dichlorocyclohexyl, methylcyclohexyl, trifluoromethylcyclohexyl, methoxycarbonylcyclohexyl, ethoxycarbonylcyclohexyl, cyclopropylmethyl, difluorocyclopropylmethyl, dichlorocyclopropylmethyl, cyclobutylmethyl, cyclopentylmethyl, cyclohexylmethyl, cyanocyclohexylmethyl, carboxycyclohexylmethyl, fluorocyclohexylmethyl, chlorocyclohexylmethyl, methylcyclohexylmethyl, trifluoromethylcyclohexylmethyl, phenyl, cyanophenyl, carboxyphenyl, nitrophenyl, fluorophenyl, chlorophenyl, bromophenyl, methylphenyl, trifluoromethylphenyl, methoxyphenyl, difluoromethoxyphenyl, trifluoromethoxyphenyl, methoxycarbonylphenyl, ethoxycarbonylphenyl, benzyl, cyanobenzyl, carboxybenzyl, fluorobenzyl, chlorobenzyl, methylbenzyl, trifluoromethylbenzyl, methoxybenzyl, difluoromethoxybenzyl, trifluoromethoxybenzyl, methoxycarbonylbenzyl, ethoxycarbonylbenzyl, furyl, tetrahydrofuryl, thienyl, tetrahydrothienyl, oxetanyl, oxazolyl, isoxazolyl.

Group 2

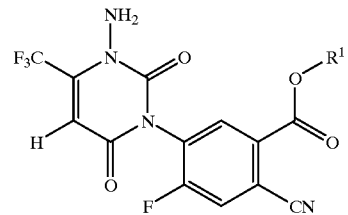

(Ib)

$R^1$ here has the meanings given above in Group 1.

Group 3

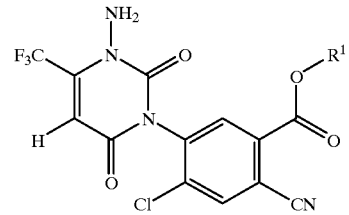

(Ic)

$R^1$ here has the meanings given above in Group 1.

Group 4

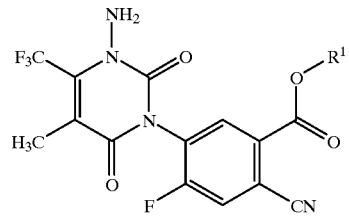

(Id)

$R^1$ here has the meanings given above in Group 1.

Group 5 (Ie)

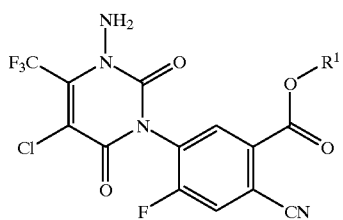

R¹ here has the meanings given above in Group 1.

Group 6 (If)

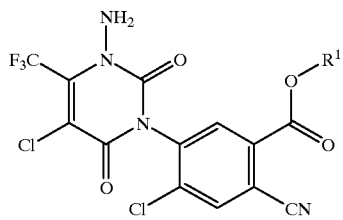

R¹ here has the meanings given above in Group 1.

Group 7 (Ig)

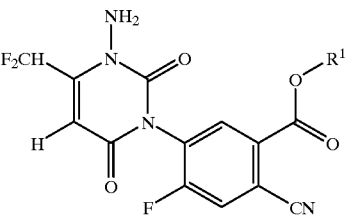

R¹ here has the meanings given above in Group 1.

Group 8 (Ih)

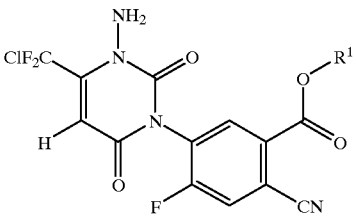

R¹ here has the meanings given above in Group 1.

Group 9 (Ik)

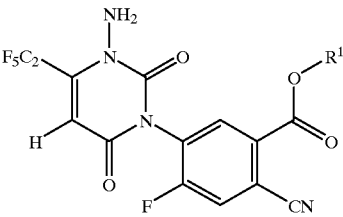

R¹ here has the meanings given above in Group 1.

Using 1-(4-cyano-3-methoxycarbonyl-phenyl)-3,6-dihydro-2,6-dioxo-4-trifluoromethyl-1(2H)-pyrimidine as starting material and 1-aminooxy-2,4-dinitro-benzene as electrophilic aminating agent, the course of the reaction in the process according to the invention can be illustrated by the following equation:

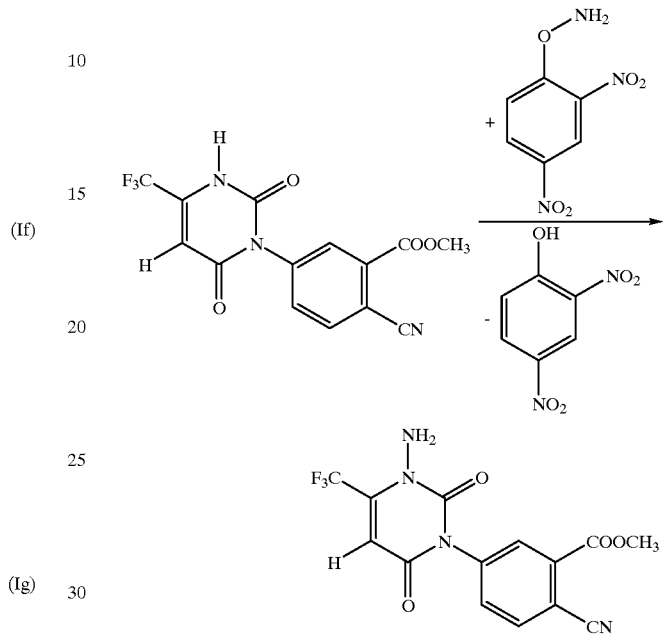

The formula (II) provides a general definition of the 1-cyanophenyl-uracils required as starting materials for carrying out the process according to the invention. In this formula, R¹, R², R³ and R⁴ each preferably or particularly preferably have those meanings which have already been mentioned in connection with the description of the substances of the formula (I) according to the invention as being preferred or as being particularly preferred for these radicals.

The 1-cyanophenyl-uracils of the formula (II) are known or can be prepared by processes known in principle (cf. EP-A 0 473 551).

Suitable electrophilic aminating agents for carrying out the process according to the invention are all customary substances which are suitable for the electrophilic introduction of an amino group. Examples include I-aminooxy-2,4-dinitro-benzene (=2,4-dinitro-phenyl-hydroxylamine) and hydroxylamine-O-sulphonic acid.

Suitable acid binders for carrying out the process according to the invention are all customary inorganic and organic bases. Preference is given to using alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium or potassium methoxide, sodium or potassium ethoxide, n- or i-propoxide, n-, i-, s- or t-butoxide; furthermore also basic organic nitrogen compounds, such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-di-methyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-di-methylamino-pyridine, N-methyl-piperidine, 1,4-diazabicyclo[2,2,2]-octane (DABCO), 1,5-diazabicyclo[4,3,0]-non-5-ene (DBN), and 1,8-diazabicyclo-[5,4,0]-undec-7-ene (DBU).

Suitable diluents for carrying out the process according to the invention are all customary inert, organic solvents. Preference is given to using aliphatic, alicyclic and aromatic, optionally halogenated hydrocarbons, such as pentane, hexane, heptane, petroleum ether, ligroin, benzine, benzene, toluene, xylene, chlorobenzene, dichlorobenzene, cyclohexane, methylcyclohexane, dichloromethane (methylene chloride), trichloromethane (chloroform) or carbon tetrachloride, furthermore dialkyl ethers, such as diethyl ether, diisopropyl ether, methyl t-butyl ether, ethyl t-butyl ether, methyl t-pentyl ether (MTBE), ethyl t-pentyl ether, tetrahydrofuran (THF), 1,4-dioxane, ethylene glycol dimethyl ether or ethylene glycol diethyl ether, diethylene glycol dimethyl ether or diethylene glycol diethyl ether; moreover dialkyl ketones, such as acetone, butanone (methyl ethyl ketone), methyl i-propyl ketone or methyl i-butyl ketone, furthermore nitriles, such as acetonitrile, propionitrile, butyronitrile or benzonitrile; furthermore amides, such as N,N-dimethylformamide (DMF), N,N-di-methyl-acetamide, N-methylformanilide, N-methylpyrrolidone or hexamethylphosphoric triamide; moreover esters, such as methyl acetate, ethyl acetate, n- or i-propyl acetate, n-, i- or s-butyl acetate; furthermore sulphoxides, such as dimethyl sulphoxide; and also alkanols, such as methanol, ethanol, n- or i-propanol, n-, i-, s- or t-butanol, ethylene glycol monomethyl ether or ethylene glycol monoethyl ether, di-ethylene glycol monomethyl ether or diethylene glycol monoethyl ether; and also mixtures thereof with water or pure water.

When carrying out the process according to the invention, the reaction temperatures can be varied within a relatively wide range. In general, the process is carried out at temperatures between −20° C. and +100° C., preferably between 0° C. and 80° C., in particular between 20° C. and 60° C.

The process according to the invention is generally carried out under atmospheric pressure. However, it is also possible to operate under elevated or reduced pressure—in general between 0.1 bar and 10 bar.

For carrying out the process according to the invention, the starting materials are generally employed in approximately equimolar amounts. However, it is also possible to employ a relatively large excess of one of the components. The reaction is generally carried out in a suitable diluent in the presence of an acid binder, and the reaction mixture is generally stirred at the required temperature for several hours. Work-up is carried out by customary methods (cf. the Preparation Examples).

The active compounds according to the invention can be used as defoliants, desiccants, haulm killers and, especially, as weed-killers. By weeds in the broadest sense, there are to be understood all plants which grow in locations where they are undesirable. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and railway tracks, and on paths and squares with or without tree plantings. Equally, the compounds can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective control of weeds in annual and perennial cultures.

The compounds of the formula (I) according to the invention are highly suitable for selectively controlling monocotyledonous and dicotyledonous weeds, both pre-emergence and post-emergence.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersing agents and/or foam-forming agents.

If the extender used is water, it is also possible to employ for example organic solvents as auxiliary solvents. Essentially, suitable liquid solvents are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersing agents are: for example lignin-sulphite waste liquors and methylcellulose.

Tackifiers such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 percent by weight of active compound, preferably between 0.5 and 90%.

For controlling weeds, the active compounds according to the invention, as such or in the form of their formulations, can also be used as mixtures with known herbicides, finished formulations or tank mixes being possible.

In some instances, synergism may occur.

Possible components for the mixtures are known herbicides, for example acetochlor, acifluorfen(-sodium), aclonifen, alachlor, alloxydim(-sodium), ametryne, amidochlor, amidosulfuron, asulam, atrazine, azimsulfuron, benazolin, benfuresate, bensulfuron(-methyl), bentazon, benzofenap, benzoylprop(-ethyl), bialaphos, bifenox, bromobutide, bromofenoxim, bromoxynil, butachlor, butylate, cafenstrole, carbetamide, chlomethoxyfen, chloramben, chloridazon, chlorimuron(-ethyl), chlomitrofen, chlorsulfuron, chlortoluron, cinmethylin, cinosulfuron, clethodim, clodinafop(-propargyl), clomazone, clopyralid, clopyrasulfuron, cloransulam(-methyl), cumyluron, cyanazine, cycloate, cyclosulfamuron, cycloxydim, cyhalofop(-butyl), 2,4-D, 2,4-DB, 2,4-DP, desmedipham, diallate, dicamba, diclofop(-methyl), difenzoquat, diflufenican, dimefuron, dimepiperate, dimethachlor, dimethametryn, dimethenamid, dinitramine, diphenamid, diquat, dithiopyr, diuron, dymron, EPTC, esprocarb, ethalfluralin, ethametsulfuron(-methyl), ethofumesate, ethoxyfen, etobenzanid, fenoxaprop-ethyl, flamprop(-isopropyl), flamprop(-isopropyl-L), flamprop(-methyl), flazasulfuron, fluazifop(-butyl), flumetsulam, flumiclorac(-pentyl), flumioxazin, flumipropyn, fluometuron, fluorochloridone, fluoroglycofen(-ethyl), flupoxam, flupropacil, flurenol, fluridone, fluroxypyr, flurprimidol, flurtamone, fomesafen, glufosinate(-ammonium), glyphosate(-isopropylammonium), halosafen, haloxyfop(-ethoxyethyl), hexazinone, imazamethabenz(-methyl), imazamethapyr, imazamox, imazapyr, imazaquin, imazethapyr, imazosulfuron, ioxynil, isopropalin, isoproturon, isoxaben, isoxaflutole, isoxapyrifop, lactofen, lenacil, linuron, MCPA, MCPP, mefenacet, metamitron, metazachlor, methabenzthiazuron, metobenzuron, metobromuron, metolachlor, metosulam, metoxuron, metribuzin, metsulfuron(-methyl), molinate, monolinuron, naproanilide, napropamide, neburon, nicosulfuron, norflurazon orbencarb, oryzalin, oxadiazon, oxyfluorfen, paraquat, pendimethalin, phenmedipham, piperophos, pretilachlor, primisulfuron(-methyl), prometryn, propachlor, propanil, propaquizafop. propyzamide, prosulfocarb, prosulfuron, pyrazolate, pyrazosulfuron(-ethyl), pyrazoxyfen, pyributicarb, pyridate, pyrithiobac(-sodium) quinchlorac, quinmerac, quizalofop(-ethyl), quizalofop(-p-tefuryl), rimsulfuron, sethoxydim, simazine, simetryn, sulcotrione, sulfentrazone, sulfometuron(-methyl), sulfosate, tebutam, tebuthiuron, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the Examples below.

PREPARATION EXAMPLES

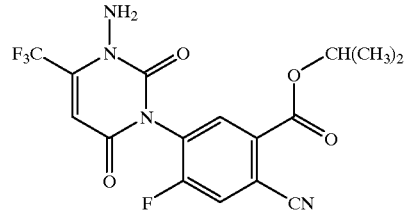

A mixture of 1.3 g (3.38 mmol) of 1-(4-cyano-2-fluoro-5-i-propoxycarbonyl-phenyl)-3,6-dihydro-2,6-dioxo-4-trifluoromethyl-1(2H)-pyrimidine, 0.76 g (3.38 mmol) of 1-aminooxy-2,4-dinitro-benzene, 0.33 g of sodium bicarbonate and 10 ml of N,N-dimethylformamide is stirred at room temperature (approximately 20° C.) for 12 days, and every second day 1.2 g of 1-aminooxy-2,4-dinitro-benzene and 1.0 g of sodium bicarbonate are added. The mixture is then poured into 0.1% strength aqueous sodium hydroxide solution and extracted with diethyl ether. The organic phase is washed first with 0.1% strength sodium hydroxide solution and then with 1N hydrochloric acid, dried with sodium sulphate and filtered. The filtrate is concentrated under waterpump vacuum, the residue is digested with 3 ml of diethyl ether and the resulting crystalline product is isolated by filtration with suction.

This gives 0.45 g (33% of theory) of 3-amino-1-(4-cyano-2-fluoro-5-i-propoxy-carbonyl-phenyl)-3,6-dihydro-2,6-dioxo-4-trifluoromethyl- 1 (2H)-pyrimidine of melting point 166° C.

Preparation of the starting material

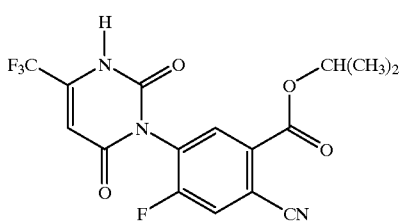

(II-1)

3.0 g (13.5 mmol) of i-propyl 5-amino-2-cyano-4-fluoro-benzoate are dissolved in 50 ml of acetone and then admixed dropwise with 3.2 g (16 mmol) of trichloro-methyl chloroformate ("diphosgene"). The mixture is stirred at room temperature for one hour and subsequently concentrated under waterpump vacuum. The residue is dissolved in toluene and then, at −30° C., added dropwise to a mixture of 3.3 g (13.5 mmol) of ethyl 3-amino-4,4,4-trifluoro-crotonate, 0.52 g of sodium hydride, 20 ml of toluene and 30 ml of N,N-dimethylformamide. The reaction mixture is stirred at −30° C. for 20 minutes and then poured into water, shaken with diethyl ether, acidified with 1N hydrochloric acid and shaken with ethyl acetate. The organic phase is washed with water, dried with sodium sulphate and filtered. The filtrate is concentrated under waterpump vacuum, the residue is digested with diethyl ether and the resulting crystalline product is isolated by filtration with suction.

This gives 1.6 g (32% of theory) of 1-(4-cyano-2-fluoro-5-i-propoxycarbonyl-phenyl)-3,6-dihydro-2,6-dioxo-4-trifluoromethyl-1(2H)-pyrimidine of melting point 120° C.

Using the methods given above, it is also possible to prepare the compounds of the formula (I) listed in Table 1 below.

TABLE 1

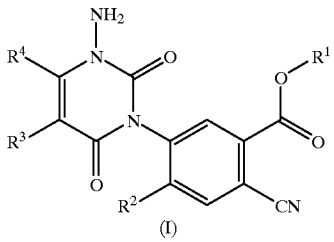

(I)

| Ex. No. | $R^1$ | $R^2$ | $R^3$ | $R^4$ | Physical data |
|---|---|---|---|---|---|
| 2 | $CH_3$ | F | H | $CF_3$ | |
| 3 | $C_2H_5$ | F | H | $CF_3$ | |
| 4 | ⌬-O | F | H | $CF_3$ | |
| 5 | $C_3H_7$-n | F | H | $CF_3$ | |
| 6 | cyclopentyl-CH₃ | F | H | $CF_3$ | |
| 7 | —CH₂—C(=O)—OC₂H₅ | F | H | $CF_3$ | |

TABLE 1-continued

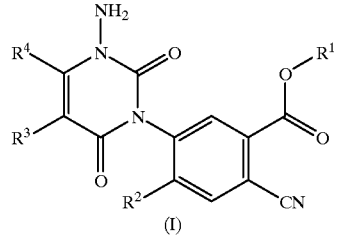

(I)

| Ex. No. | $R^1$ | $R^2$ | $R^3$ | $R^4$ | Physical data |
|---|---|---|---|---|---|
| 8 | —CH₂—C(=O)—OCH₃ | F | H | $CF_3$ | |
| 9 | —CH(CH₃)—C(=O)—OC₂H₅ | F | H | $CF_3$ | |
| 10 | —CH(CH₃)—C(=O)—OCH₃ | F | H | $CF_3$ | |
| 11 | ⌬-O (oxetanyl) | Cl | H | $CF_3$ | |
| 12 | $C_3H_7$-i | H | H | $CF_3$ | |
| 13 | —OCH₂CH₂OCH₃ | F | H | $CF_3$ | |
| 14 | —CH₂—CH=CH₂ | F | H | $CF_3$ | |
| 15 | —CH₂-cyclopentyl | F | H | $CF_3$ | |
| 16 | —CH₂—C(=O)—O-alkyl | F | H | $CF_3$ | |
| 17 | —CH₂—C(=O)—O-alkyl | H | H | $CF_3$ | |
| 18 | —CH(CH₃)—C(=O)—O-alkyl | F | H | $CF_3$ | |
| 19 | —CH(CH₃)—C(=O)—O-alkyl | H | H | $CF_3$ | |

Use Examples

Example A

Pre-emergence Test
Solvent: 5 parts by weight of acetone
Emulsifier: 1 part by weight of alkylaryl polyglycol ether
To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After approximately 24 hours, the soil is sprayed with the preparation of the active compound in such a way as to apply the particular mixed amounts of active compound per unit area. The concentration of the spray liquor is chosen so that the particular amounts of active compound desired are applied in 1 000 l of water/ha.

After three weeks, the degree of damage to the plants is rated in % damage in comparison to the development of the untreated control.

The figures denote:

0%=no effect (like untreated control)

100%=total destruction

In this test, the compound of Preparation Example 1 exhibits, at an application rate of 30 g/ha, an activity of more than 90% against several weeds.

amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

0%=no effect (like untreated control)

100%=total destruction

In this test, the compound of Preparation Example 1 exhibits, at an application rate of 30 g/ha, an effect of 100% against several weeds.

TABLE A

Pre-emergence-Test/Greenhouse

| Compound of Preparation Example | Application rate (g of ai./ha) | Echinochloa | Sorghum | Abutilon | Datura | Matricaria |
|---|---|---|---|---|---|---|
| 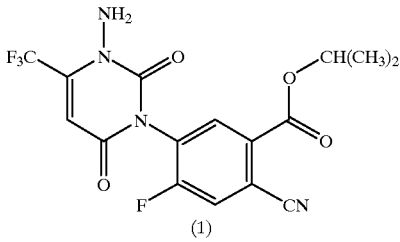 (1) | 30 | 100 | 95 | 100 | 100 | 100 |

Example B

Post-emergence Test

Solvent: 5 parts by weight of acetone

Emulsifier: 1 part by weight of alkylaryl polyglycol ether

To produce a suitable preparation of active compound, 1 part by weight of active compound is mixed with the stated

TABLE B

Post-emergence Test/Greenhouse

| Compound of Preparation Example | Application rate (g of ai./ha) | Alopecurus | Bromus | Setaria | Abutilon | Datura | Matricaria |
|---|---|---|---|---|---|---|---|
| 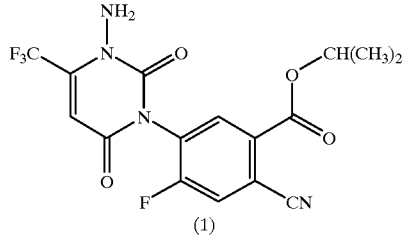 (1) | 30 | 100 | 100 | 100 | 100 | 100 | 100 |

What is claimed is:

1. A compound of the formula

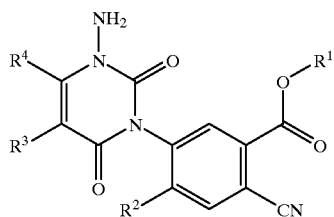

(I)

wherein
- $R^1$ represents hydrogen or represents unsubstituted or cyano-, carboxyl-, halogen-, $C_1$–$C_4$-alkoxy- or $C_1$–$C_4$-alkoxy-carbonyl-substituted alkyl having 1 to 6 carbon atoms or
  represents in each case unsubstituted or cyano-, carboxyl- or $C_1$–$C_4$-alkoxy-carbonyl-substituted alkenyl or alkynyl having in each case 2 to 6 carbon atoms, or
  represents cycloalkyl or cycloalkylalkyl having in each case 3 to 6 carbon atoms in the cycloalkyl group and 1 to 4 atoms in the alkyl moiety and being in each case unsubstituted or mono- to tetrasubstituted by identical or different substituents selected from the group consisting of cyano, carboxyl, halogen, $C_1$–$C_4$-alkyl and $C_1$–$C_4$-alkoxy-carbonyl, or
  represents aryl or arylalkyl having 6 or 10 carbon atoms in the aryl group and 1 to 4 carbon atoms in the alkyl moiety and being in each case unsubstituted or mono- to trisubstituted by identical or different substituents selected from the group consisting of nitro, cyano, carboxyl, halogen, $C_1$–$C_4$-alkyl, halogeno-$C_1$–$C_4$-alkyl, $C_1$–$C_4$-alkoxy, halogeno-$C_1$–$C_4$-alkoxy and $C_1$–$C_4$-alkoxy-carbonyl, or
  represents heterocyclyl or heterocyclylalkyl which is selected from the group consisting of oxetanyl, furyl, furylmethyl, tetrahydrofuryl, tetrahydrofurylmethyl, thienyl, oxazolyl, isoxazolyl, thiazolyl, pyrazolyl, oxadiazolyl, pyridinyl, pyridinylmethyl, each of which is unsubstituted or mono- to trisubstituted by identical or different substituents selected from the group consisting of cyano, carboxyl, halogen, $C_1$–$C_4$-alkyl, halogeno-$C_1$–$C_4$-alkyl, $C_1$–$C_4$-alkoxy and halogeno-$C_1$–$C_4$-alkoxy,
- $R^2$ represents hydrogen, cyano or halogen,
- $R^3$ represents hydrogen, fluorine, chlorine, bromine or represents alkyl having 1 to 4 carbon atoms which is unsubstituted or mono- to pentasubstituted by identical or different substituents selected from the group consisting of fluorine, chlorine and bromine, and
- $R^4$ represents alkyl having 1 to 4 carbon atoms or represents halogenoalkyl having 1 to 4 carbon atoms and 1 to 5 halogen atoms selected from the group consisting of fluorine, chlorine, and bromine.

2. A compound of the formula

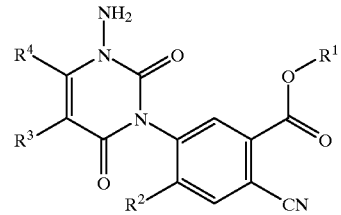

(I)

wherein
- $R^1$, $R^3$, and $R^4$ are as defined in claim 8, and
- $R^2$ represents hydrogen, cyano, fluorine, chlorine or bromine.

3. A herbicidal composition, comprising at least one compound of the formula (I) according to claim 1 and one or more extenders and/or surfactants.

4. A method for controlling weeds, comprising the step of applying a compound of the formula (I) according to claim 1 to the weeds and/or their habitat.

5. A process for preparing a herbicidal composition, comprising the step of mixing a compound of the formula (I) according to claim 1 with extenders and/or surfactants.

* * * * *